United States Patent [19]

Schmidt

[11] 4,248,822

[45] Feb. 3, 1981

[54] PROCESS AND APPARATUS FOR PRODUCING A MOISTURE-PERMEABLE FILM

[75] Inventor: Theo Schmidt, Forchheim, Fed. Rep. of Germany

[73] Assignee: Lever Brothers Company, New York, N.Y.

[21] Appl. No.: 11,473

[22] Filed: Feb. 12, 1979

[30] Foreign Application Priority Data

Feb. 15, 1978 [DE] Fed. Rep. of Germany ....... 2806402

[51] Int. Cl.³ .............................................. B29C 17/08
[52] U.S. Cl. .................................... 264/154; 264/156; 264/230; 264/287; 264/DIG. 71; 425/290; 425/302.1; 425/343; 425/363; 425/DIG. 37
[58] Field of Search ............... 264/154, 156, 282, 230, 264/DIG. 71, 287; 425/302.1, 336, 343, 363, DIG. 37, 290

[56] References Cited

U.S. PATENT DOCUMENTS

| | | | |
|---|---|---|---|
| 3,012,918 | 12/1961 | Schaar | 264/156 X |
| 3,092,439 | 6/1963 | Harrison | 264/156 X |
| 3,132,985 | 5/1964 | Moore | 264/156 X |
| 3,146,283 | 8/1964 | Da Valle | 264/156 |
| 3,356,562 | 12/1967 | Graham et al. | 264/282 X |
| 3,384,696 | 5/1968 | Makansi | 264/156 X |
| 3,673,839 | 7/1972 | Nielsen et al. | 264/282 X |

FOREIGN PATENT DOCUMENTS

848800 9/1960 United Kingdom .
851473 10/1960 United Kingdom .

*Primary Examiner*—Philip Anderson

[57] ABSTRACT

In the manufacture of a moisture-permeable covering film for absorbent material a thermoplastic film is provided with capillary-like protrusions by embossing, after which openings are produced in the ends of said protrusions. Embossing is effected with simultaneous cooling of the film, so that the ends of the protrusions are oriented in the thermo-elastic temperature range. By a renewed heating of the ends of the protrusions the openings are formed by shrinking, which also causes the edges of the openings to be thickened.

The apparatus consists of an engraved metal cylinder and a counter-roller for the embossing step and of a heated roller, which is pressed against the ends of the embossed protrusions on the metal cylinder.

7 Claims, 13 Drawing Figures

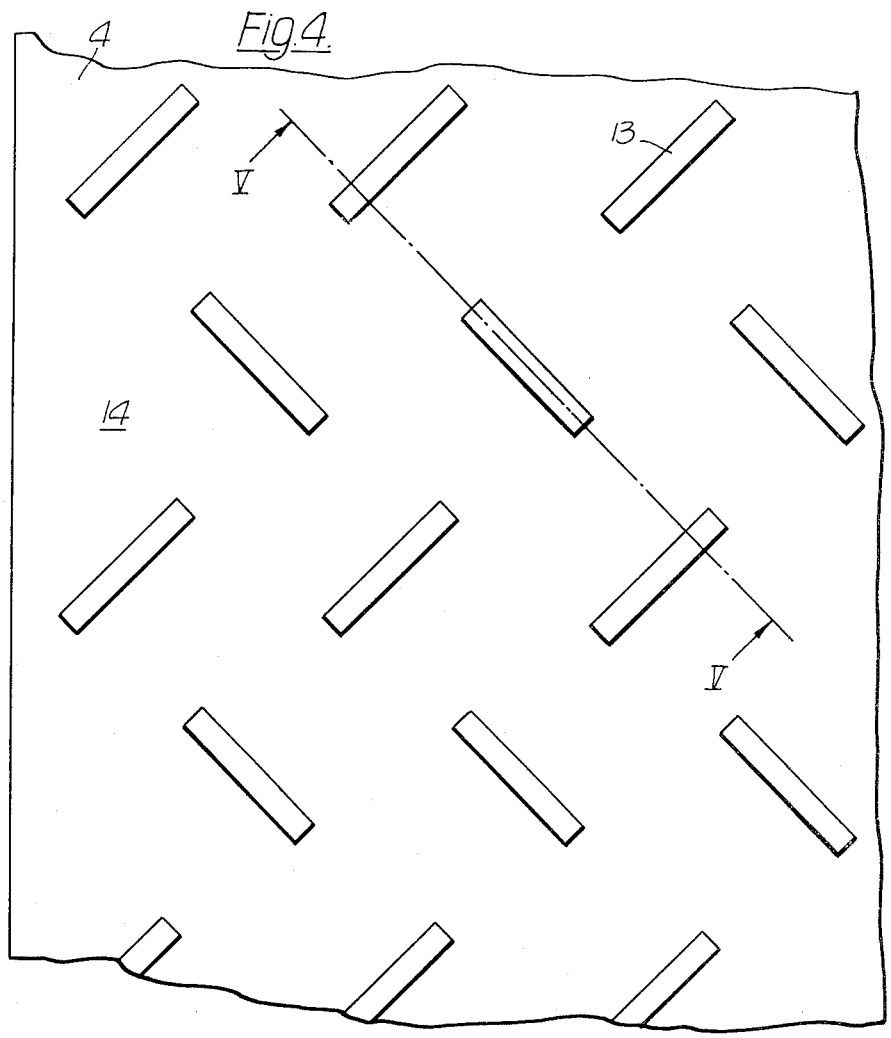
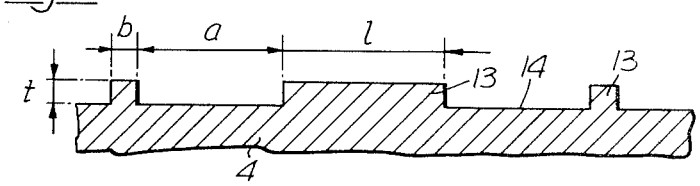

PROCESS AND APPARATUS FOR PRODUCING A MOISTURE-PERMEABLE FILM

PROCESS AND APPARATUS FOR PRODUCING A MOISTURE-PERMEABLE FILM

The invention relates to a process and an apparatus for manufacturing a film which is permeable to moisture and liquids. The film consists of a thermoplastic material which in itself is impermeable to liquids and is provided with protrusions which at their ends have openings for the passing of liquids. The film is particularly suitable as covering film for an absorbent material and in combination with such a material the film is semi-permeable, in that the liquid only passes or is sucked through the film in the direction of the absorbent material.

In German patent application No. 2 556 501 corresponding to U.S. Pat. No. 3,929,135 a similar film is described as covering layer for a disposable napkin, in which the film is provided with so-called tapered capillaries which have an approximately conical shape and the apex of which, protruding from the plane of the film, contains a small opening. In this publication also several processes are mentioned for manufacturing such a film. Thus, it is possible to form the film by means of a heatable mould, provided with thorns, and a flexible plate and simultaneously punch it, or such a film is deep-drawn by vacuum-deformation with the aid of a suitable moulding plate. According to a further process the film can be moulded in a mould provided with thorns. If desired, the film provided with the deformations can still be processed in such a way that material is removed from the apexes to bring the diameter of the openings to the value aimed at. This processing can be effected by grinding off the apexes or by heating the film in order to melt the apexes.

These processes seem to be inefficient for large scale manufacture.

British Patent Specification No. 851 473 describes a process in which a film is passed over a cooled perforated cylinder and a jet of heated air is directed on to the film, so that the areas of the film located over the perforated holes of the cylinder are melted. The perforation holes of the film are reinforced at their periphery by the molten material. This film, however, is not suitable for use as a semi-permeable covering film, since the openings lie in the plane of the film and thus no capillaries are formed.

The object of the invention is to improve the manufacture of permeable films, in that the films are provided with protrusions ending in openings through which the liquid can be sucked in as through a capillary, by an absorbent material.

According to the invention a starting film from thermoplastic material is first heated to a deformation temperature near the lower limit of the thermoplastic temperature range of the material. At this temperature the film is introduced into an embossing nip and during embossing is deformed with simultaneous cooling in the thermo-elastic temperature range, during which the protrusions are formed. The embossing nip is formed between a cooled and engraved metal cylinder and a counter-roller. The counter-roller can have have an elastic surface, into which the elevations graved in the metal cylinder press in during operation, or it may be provided with a negatively engraved cylinder. Behind the embossing nip the embossed film, bearing on the metal cylinder, is further cooled and subsequently the ends of the protrusions are heated for a short time at or above the temperature applied on deformation for shrinking the ends of the protrusions, resulting in the openings being formed. The deformation of the film in the embossing nip is advantageously effected in such a way that the ends of the protrusions are shaped with simultaneous localized cooling an stretched, whereas the stretching experienced by the base surface of the film is insignificant. Owing to this stretching, particularly of the ends of the protrusions, the material in the end surfaces is oriented, which on renewed heating to or above the initial deformation temperature leads to shrinking. As a result of the shrinking the end surfaces tear open, and thickenings form around the edges of the openings, reinforcing the latter. The renewed heating of the end surfaces is suitably effected by contact heat from a hot roller pressed against the engraved and cooled metal cylinder. The roller heats only the end surfaces themselves. The side walls of the protrusions further bear on the cooled engraved metal cylinder and practically cannot shrink. After further cooling the film can be removed from the engraved cooled metal cylinder, if desired further cooled and wound up.

The apparatus according to the invention for carrying out the process described before consists of an embossing device, known per se, in which an embossing nip is formed between an engraved metal cylinder and a counter-roller, e.g. in the form of a roller with an elastic surface from rubber or a similar material. Both the engraved metal cylinder and the counter-roller are cooled. Also after the embossing step the film is led on to the engraved metal cylinder over part of its circumference. Before the spot on which the film is taken off from the metal cylinder a heated roller is arranged, which can be pressed against the film on the metal cylinder. The purpose of this heated roller is to heat the end surfaces of the protrusions for a short period to such a degree that they shrink to form openings. The surface temperature of the heated roller therefore is about the deformation temperature of the film or even exceeds it and lies in the thermoplastic temperature range of the material. The heated roller is pressed against the metal cylinder at a considerable pressure. This pressing is effected at a pressure of 1 to 2 N/mm (i.e. 1 to 2 Newton per mm of the line of contact between the metal cylinder and the heated roller). The high temperature of the heated roller and its pressure ensure a rapid transmission of heat and thus a sudden heating of the end surfaces to the shrinking temperature, also in the case of film speeds exceeding 100 m/min., at which the contact time between the end surfaces and the heated roller is extremely short. The higher the film speed, the higher the pressure and the surface temperature of the heated roller should be.

The invention will be illustrated with reference to the examples shown in the drawings, in which:

FIG. 4 is a view on part of the surface unwound from the engraved cylinder, showing a preferred pattern of bosses;

FIG. 5 is a section through the engraved cylinder surface, according to FIG. 4;

Figure 1:
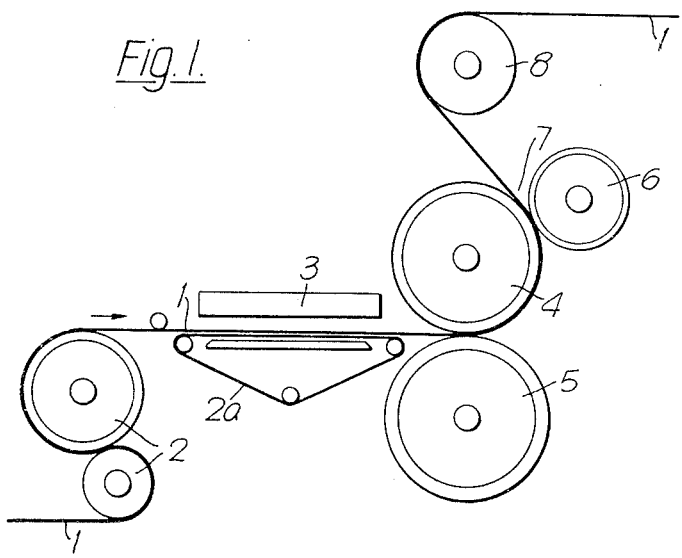
FIG. 1 is a diagram showing the travelling of the film through an apparatus.

In the example shown, the film 1, coming directly from an extruder or calender or from a supply roll, which are not shown, is passed by guiding means, such as roller 2 and a conveying device 2a to a heating device 3 and gets from the latter into the embossing nip between the engraved cooled cylinder 4 and the counter-roller 5, which possesses a rubber-elastic surface and is also cooled. The embossed film 1 runs over part, at least about 30°, of tube circumference of the engraved cylinder 4. The ends of the protrusions come into contact with the heated roller 6, resulting in the formation of openings. After a further cooling on the cylinder 4 the film is taken off at spot 7 from the cylinder and passed over an end roller 8 to further cooling rollers (not shown) and a winding device (not shown). The cylinder 4 and the rollers 5, 6 and 8 can be supported in a conventional way in a frame. Conventional devices can be used for setting the required temperatures of cylinder and rollers. Suitably the roller 8 is used for the further cooling of the film. The heated roller 6 is supported in such a way that it can be pressed against the metal cylinder 4 with an adjustable pressure of 1 to 2 N/mm of contact line with the metal cylinder, or even a higher pressure.

Figure 2:
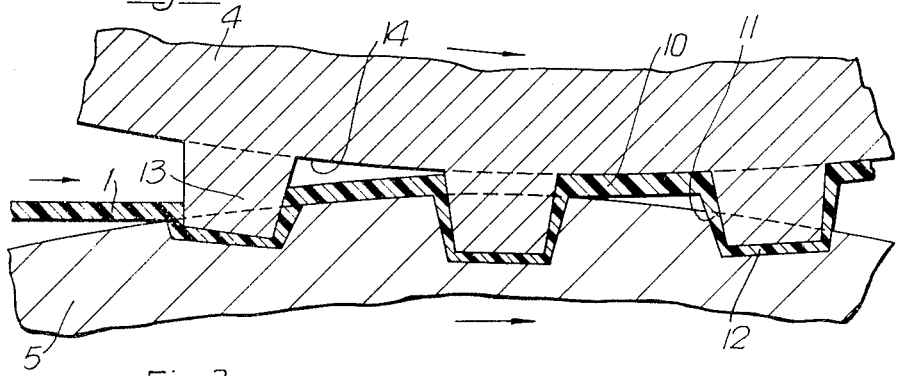
FIG. 2 is a section through the embossing nip, in which the protrusions are formed.

FIG. 2 shows the embossing of a film 1 from low-density polyethylene in the embossing nip between the metal cylinder 4 and the counter-roller 5 with elastic surface. The film runs onto the counter-roller 5. It is pressed into the elastic surface of the counter-roller 5 by the bosses 13, which as a result of the engraving project from the circumferential surface of the metal cylinder 4. In this step the film, which had previously been heated close to the thermoplastic temperature range or about its melting point, cools down in accordance with the intensity with which it comes into contact with the cold parts of the apparatus, such as the boss 13 and the surface of the cooled elastic counter-roller 5. This leads to the end surface 12 and partly also the sides 11 of the protrusion being stretched at a lower temperature, accompanied by an orientation as well as a decrease in thickness of the material. In this embossing step the non-embossed parts 10 of the film retain their original thickness and cool down more slowly. The protrusions are embossed to such a shape that the ends are flat surfaces extending parallel to the base surface of the embossed film or that the ends are only slightly curved.

Figure 3:
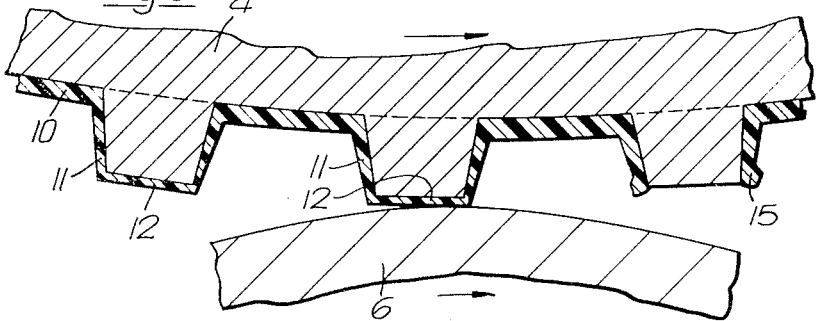
FIG. 3 is a section through the contact zone between engraved cylinder and heated roller, in which the ends of the protrusions are shrunk to form openings.

After all parts of the embossed film have cooled to about the surface temperature of the metal cylinder, the end surfaces 12 of the protrusions come into contact with the heated roller 6, as shown in FIG. 3. As a result of the re-heating to the deformation temperature or even higher, the end surfaces 12 immediately shrink after contacting the heated roller 6, with formation of openings, while the film with the protrusions embossed in it is still being supported by the embossing metal cylinder. The shrinking material causes beads 15 to form around the openings. As there is only a short contact between the heated roller 6 and the end surface 12 or only part of the area of the end surface 12, no shrinking of the side walls 11 takes place. Besides, these side walls still bear on the cooled metal cylinder and also for this reason do not essentially change form.

In an experimental arrangement the surface temperatures of the metal cylinder 4 and of the elastic counter-roller 5 were about 60° C. or lower. The metal cylinder 4 had a diameter of 320 mm. The diameter of the counter-roller 5 was slightly larger. In the arrangement the length of the rollers was 600 mm. The diameter of the heated roller 6 was about 150 mm. The surface temperature was adjustable from 100° C. to about 200° C. In the case of low film speeds the surface was heated at about 145°. For film speeds exceeding 200 m/min the surface temperature was at least 170° C. at a pressure of the rollers 6 against the metal cylinder 4 of about 1.37 N/mm. The peripheral velocities of the metal cylinder 4 of the counter-roller 5 and the heated roller 6 were nearly equal.

A film 1 from hard-PVC was introduced at a temperature in the thermo-elastic range, but below the thermoplastic temperature range, i.e. suitably a deformation temperature of over 150° C., into the embossing nip, was cooled by the two cooled embossing rollers 4 and 5, in which step the end surfaces 12 were shaped and simultaneously oriented at temperatures between about 90° and 140° C., and after further cooling of the embossed film shrinking of the end surfaces 12 was effected by a sudden heating at 100° to 140° C. by contact with the heated roller 6. In the case of partly crystalline plastics such as e.g. polyethylene, the films were heated to about their melting point, the ends of the protrusions were then shaped below this melting point with simultaneous cooling, the films, bearing further on the cooled engraved melting cylinder, were then cooled to below the crystalline melting point, e.g. to about 60° C., and thereafter, by a sudden reheating of the end surfaces up to the melting point, the openings were produced by shrinking.

Although for a sudden heating of the end surfaces it may be necessary to hold the surface temperature of the heated roller 6 at 150° to nearly 200° C., melting of the material of the end surfaces 12 should be avoided as much as possible, since in that case the material of the film would stick to the heated roller 6.

The engraving of the metal cylinder 4 can be effected by means of gravers or by another known process. The surface of the heated roller 6 can consist of steel or of lead. In order to compensate for deflections of the heated roller 6 as well as of the metal cylinder 4 and for unevennesses, which may be inevitable in engravings, the surface of the heated roller 6 can be made elastic. The surface can be provided with a silicone layer, a layer from polytetrafluoroethylene or a similar material which on the one hand is elastic and on the other hand reduces the adhering of any melting particles of the film to said surface.

According to the process starting films with a thickness of 0.02 to 0.06 mm and, if desired, of more than 0.1 mm are used. As material for the film all thermoplastics can be considered. In particular polyethylene, polypropylene, polyvinylchloride and their thermoplastic copolymers are used. A preferred material is low-density polyethylene.

The size of the openings to be produced is dependent on the viscosity of the liquid passing through. The openings should at least have a free circular cross-section of 0.1 mm diameter. Protrusions and openings may have any shape desired and may be circular, square, slit-shaped, triangular or star-shaped. In a preferred embodiment with slit shaped openings the protrusions have a length that is 5 to 30 times, particularly 5 to 8 times their width. Preferred openings have a cross-section of 0.2 by 6 mm, preferably 0.3 by 2 mm. The depth of the protrusions, i.e. the height of the side walls 11, should be at least as large as the smallest width of the openings. For the preferred slit-shaped openings of 0.3 by 2.0 mm the protrusions have a depth of 0.3 mm.

The cross-section of the protrusions can decrease towards the opening, so that for a circular opening e.g. a conical protrusion is provided. If the protrusions have a conical shape with a corresponding shape of the engravings or bosses on the metal cylinder, the size of the openings can also be affected by the choice of the elastic coating of the heated roller and its pressure. Preferably however the protrusions are given such a shape that their side walls project from the base film at about right angles and the cross-section over the total height of the protrusion is essentially constant. By means of this form a capillary action can be obtained over the entire length of the protrusion and thus an improved suction of moisture.

In the preferred embodiment shown in FIG. 4 the bosses 13 produced by engraving have the cross-section of narrow rectangles. The bosses 13 have been arranged at an angle of about 45° to the peripheral direction of the cylinder, the inclination varying from row to row. A corresponding image is shown by the film produced. This arrangement of the protrusions and slits results in a sufficiently coherent base surface 10 of the film 1, so that also in the case of higher web tensions the film can be further processed without difficulties because by this pattern of slits a sufficient tensile strength in each direction is obtained.

FIG. 5 shows a section through the surface of the engraved metal cylinder. If such a cylinder is used, the cross-sections of the embossments are equal over their depth and the inner surface of the side walls 11 extends at a right angle to the base surfaces 10. Preferred dimensions for the bosses 13 of the engraved cylinder and correspondingly for the protrusions are t=0.3 mm, b=0.3 mm, l=2.0 mm. The distance a is nearly 1.75 mm.

Figure 6:
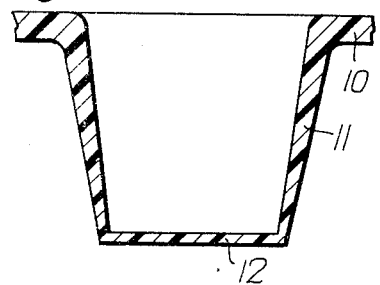
FIGS. 6 and 6a to 9 and 9a are sections through protrusions before and after the production of the openings at the ends of the protrusions.
Figure 6A:
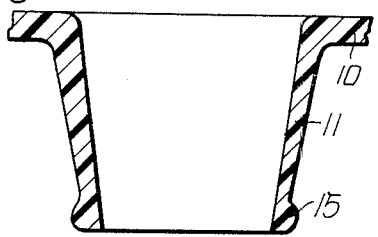
Figure 7:
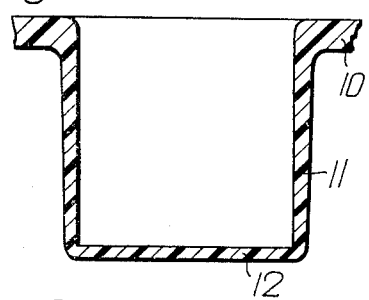
Figure 7A:
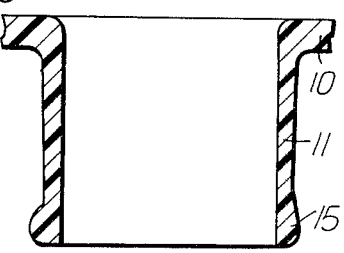

FIGS. 6 to 9 show various possible cross-sectional shapes of the protrusions. The use of a tool according to FIG. 5 results in a protrusion according to FIG. 7 and after producing the opening from the end surface 12 a capillary is formed as shown in FIG. 7a, the cross-section of which is constant over its entire length and the opening of which has been reinforced by a bead 15 lying outside on the side walls 11. By this process, however, also tapered capillaries as shown in FIG. 6a can be produced, in which case, too, the bead can lie on the outside.

Figure 8:
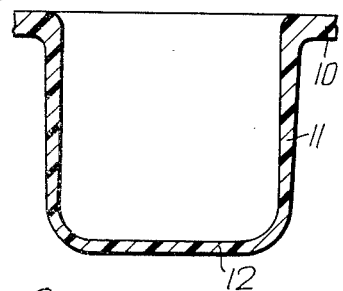
Figure 8A:
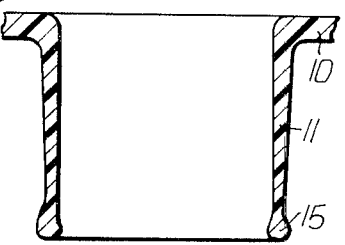
Figure 9:
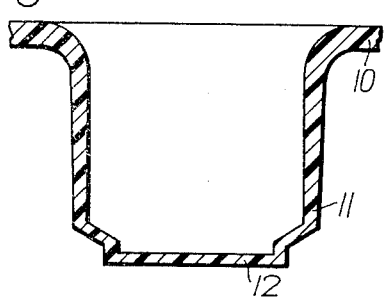
Figure 9A:
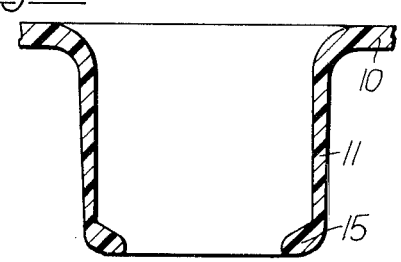

By a corresponding shaping of the bosses 13 on the engraved cylinder, however, also beads as shown in FIGS. 8 and 9 can be produced in such a way that they penetrate more or less into the passage cross-section of the capillary. FIG. 9, moreover, shows a more strongly rounded transition between the base surface 10 and the side wall 11.

I claim:

1. A process for manufacturing a moisture-permeable film from a thermoplastic material, comprising heating a moisture-impermeable film of a thermoplastic material to a deformation temperature near the lower limit of the thermoplastic temperature range at which deformation temperature orientation may be achieved while continuously advancing said film, embossing small protrusions in said heated film with such a shape that the end surfaces of the protrusions are flat surfaces which extend parallel to the base surface of said film and such that at least the end surfaces of the protrusions are oriented, cooling said embossed film while embossing said film and then further cooling said film, subsequently heating the end surfaces of the protrusions for a short time to at least the deformation temperature of the film material and thereby shrinking the end surfaces to form openings at the ends of the protrusions while supporting said embossed film on a cooled embossing cylinder.

2. A process according to claim 1, comprising shrinking the ends of the protrusions by heating said ends and simultaneously cooling the side walls of the protrusions and thereby forming thickened and strengthened edges around the openings.

3. A process according to claim 1, comprising embossing of the starting film with slit-shaped protrusions which have a length being 5 to 30 times their width and are arranged in rows staggered and in alternating direction.

4. An apparatus comprising an embossing device, in which an embossing nip is formed between an engraved metal cylinder and a counter-roller, which metal cylinder and counter-roller are cooled, and a heated roller, which can be pressed against the tops of the bosses of the engraved metal cylinder, and means for guiding the heated starting film into the embossing nip and for taking off the embossed film provided with openings in the ends of the protrusions from the metal cylinder.

5. An apparatus according to claim 4 comprising a heated roller, the surface temperature of which lies in the thermoplastic temperature range of the thermoplastic material of the film.

6. An apparatus according to claim 5 comprising a heated roller having an elastic surface.

7. An apparatus according to claim 4 in which the heated roller is pressed against the metal cylinder with a pressure of 1 to 2 N per mm of length of the line of contact between metal cylinder and heated roller.

* * * * *